(12) United States Patent
Erickson

(10) Patent No.: US 9,839,681 B1
(45) Date of Patent: *Dec. 12, 2017

(54) SIZE TUNABLE MICROBIAL MIMETICS FOR IMMUNOTHERAPY OF CANCER

(71) Applicant: Timothy Andrew Erickson, Beaverton, OR (US)

(72) Inventor: Timothy Andrew Erickson, Beaverton, OR (US)

(73) Assignee: Timothy Andrew Erickson, Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/635,069

(22) Filed: Jun. 27, 2017

Related U.S. Application Data

(60) Provisional application No. 62/474,926, filed on Mar. 22, 2017.

(51) Int. Cl.
*A61K 39/00* (2006.01)

(52) U.S. Cl.
CPC ...... *A61K 39/0011* (2013.01); *A61K 2039/53* (2013.01); *A61K 2039/54* (2013.01); *A61K 2039/585* (2013.01)

(58) Field of Classification Search
None
See application file for complete search history.

*Primary Examiner* — Brad Duffy

(57) ABSTRACT

This invention describes novel immunogenic complexes, which are designed to trigger a robust host immune response against cancer cells by co-opting the immune system's natural ability to eliminate pathogen-infected host cells. The immunogenic complexes, referred to as microbial mimetics (MM) have unique physical and biochemical properties, which are designed to simulate a pathogenic infection of similar sized bacteria and viruses, permitting tumor-associated and tumor-specific peptide antigens to be presented to immune cells as microbial constituents. The MM are well-suited to mimic a systemic infection with microbe sized particles comprised largely of tumor antigens. Under this framework, tumor cells may be eliminated in the ensuing immune response.

The MM exhibit unique properties, including size tunability and contain antigenic cargo complexed to immune stimulatory molecules, which synergize to potentiate immune responses. The MM constitute a versatile platform for triggering immune responses against cells expressing epitopes contained within the complexed antigenic cargo.

16 Claims, 14 Drawing Sheets

SEQUENCE LISTING

```
<160> NUMBER OF SEQ ID NOS: 8

<210> SEQ ID NO 1
<211> LENGTH: 20
<212> TYPE: RNA
<213> ORGANISM: Artificial Sequence
<220> FEATURE:
<223> OTHER INFORMATION: RNA248, a synthetic RNA sequence

<400> SEQUENCE: 1
guuggugguu gugugagcgu                                               20

<210> SEQ ID NO 2
<211> LENGTH: 22
<212> TYPE: DNA
<213> ORGANISM: Artificial Sequence
<220> FEATURE:
<223> OTHER INFORMATION: DNA4, a synthetic DNA sequence

<400> SEQUENCE: 2
tcgtcggttt cggcgcgcgc cg                                            22

<210> SEQ ID NO 3
<211> LENGTH: 26
<212> TYPE: DNA
<213> ORGANISM: Artificial Sequence
<220> FEATURE:
<223> OTHER INFORMATION: DNA10, a synthetic DNA sequence

<400> SEQUENCE: 3
ttcggcgcgc gcgcgcgcgc gccgtt                                        26

<210> SEQ ID NO 4
<211> LENGTH: 31
<212> TYPE: PRT
<213> ORGANISM: Artificial Sequence
<220> FEATURE:
```

-continued

```
<223> OTHER INFORMATION: Linker Sequence + synthetic peptide
      corresponding to calcitonin

<400> SEQUENCE: 4

Arg Arg His Arg Lys Arg Arg Leu Ser Thr Cys Met Leu Gly Thr Tyr
1               5                   10                  15

Thr Gln Asp Phe Asn Lys Phe His Thr Phe Pro Gln Thr Ala Ile
            20                  25                  30

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide corresponding to Trp2 gene +
      Linker Sequence

<400> SEQUENCE: 5

Ser Val Tyr Asp Phe Phe Val Trp Leu Arg Arg His Arg Lys Arg Arg
1               5                   10                  15

<210> SEQ ID NO 6
<211> LENGTH: 22
<212> TYPE: PRT
<213> ORGANISM: Artificial Sequence
<220> FEATURE:
<223> OTHER INFORMATION: Synthetic peptide corresponding to Trp2 gene +
      Linker Sequence
<220> FEATURE:
<221> NAME/KEY: LIPID
<222> LOCATION: (1)..(1)
<223> OTHER INFORMATION: Cys at N-terminus lipidated using two palmitic
      acid residues

<400> SEQUENCE: 6

Cys Ser Lys Lys Lys Lys Ser Val Tyr Asp Phe Phe Val Trp Leu Arg
1               5                   10                  15

Arg His Arg Lys Arg Arg
            20

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide Linker Sequence

<400> SEQUENCE: 7

Arg Arg His Arg Lys Arg Arg
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide corresponding to Trp2 gene

<400> SEQUENCE: 8

Ser Val Tyr Asp Phe Phe Val Trp Leu
1               5
```

SIZE TUNABLE MICROBIAL MIMETICS FOR IMMUNOTHERAPY OF CANCER

RELATED U.S. APPLICATION DATA

This application claims priority to U.S. Provisional Application No. 62/474,926, filed on Mar. 22, 2017, and cross-references U.S. patent application Ser. No. 15/631,843, filed on Jun. 23, 2017, and U.S. patent application Ser. No. 15/436,525, filed on Feb. 17, 2017.

REFERENCES CITED

U.S. Patent Documents

U.S. Pat. No. 5,662,907 A September 1997 Kubo et al.
U.S. Pat. No. 6,727,230 A April 2004 Hutcherson et al.

OTHER PUBLICATIONS

Erhard, Michael H., et al. "lipopeptide, Pam2Cys-Ser-(Lys) 4: an alternative adjuvant to Freund's adjuvant for the immunisation of chicken to produce egg yolk antibodies." *Alternatives to laboratory animals: ATLA* (1997).

Zeng, Weiguang, David C. Jackson, and Keith Rose. "Synthesis of a New Template with a Built-in Adjuvant and Its Use in Constructing Peptide Vaccine Candidates Through Polyoxime Chemistry." *Journal of Peptide Science* 2.1 (1996): 66-72.

Deres, Karl, et al, "In vivo priming of virus-specific cytotoxic T lymphocytes with synthetic lipopeptide vaccine." *Nature* 342.6249 (1989): 561-564.

FIELD OF INVENTION

Embodiments herein relate to treatments for cancer, and more specifically to immunogenic complexes with enhanced physical and chemical properties for eliciting a host immune response against solid tumors.

RELATED U.S. APPLICATION DATA

This application claims priority to U.S. Provisional Application No. 62/474,926, filed on Mar. 22, 2017, and cross-references U.S. patent application Ser. No. 15/631,843, filed on Jun. 23, 2017, and U.S. patent application Ser. No. 15/436,525 filed on Feb. 17, 2017.

BACKGROUND OF THE INVENTION

Current Standard of Care of Metastatic Cancer

Metastatic cancers are often fatal, affecting persons of all ages and backgrounds. While great advances in patient care have been realized in recent years by employing novel agents, such as molecular targeted therapies and immune checkpoint inhibitors, the majority of metastatic (Stage IV) cancers are currently incurable. Thus, novel approaches are needed to improve outcomes for patients with metastatic disease, which is refractory to existing therapies.

Rationale for Employing Novel Immunotherapeutic Approaches to Treat Solid Tumors A strategy for improving treatment of human cancers, is to provoke a robust and targeted cellular immune response against cells expressing tumor-specific antigens and tumor-associated antigens, for example by administration of an immunogenic composition that elicits an immune response targeting the cancer cells. For the purposes of this disclosure, tumor-specific antigens are defined as antigens (specific amino acid sequences) that are exclusively expressed in tumor cells, whereas tumor-associated antigens are defined as antigens, which are putatively expressed only in the organ from which the founder cancer cell originates.

Targeting of Non-Vital Cells Using Tissue Restricted Antigens

While engaging the immune system to eradicate cells expressing tumor-specific antigens offers an exquisitely high therapeutic index whereby only cancer cells are targeted for elimination, eliciting immune-mediated destruction of cells expressing tumor-associated antigens (self-antigens) implies provoking targeted autoimmune disease, and there are inherent risks. In the case of tumor-associated antigens, only antigens present in cells not critical to sustaining life may be safely targeted. Therefore, ubiquitously expressed antigens, or antigens normally expressed in vital organs, such as the brain, liver, kidneys, lungs, immune cells and bone marrow cannot be safely targeted.

However, due to tissue restricted antigen expression, cells expressing certain self-antigens can be targeted with some margin of safety. For instance, the thyroid, ovaries, prostate, and breast tissue all have important functions, but patients can survive without these organs. Additionally, non-synonymous coding mutations, which make cancer cells genetically distinct from their host, also function as viable tumor-specific targets.

Fulfilling an Unmet Clinical Need

In recent years, the field of cancer immunotherapy has witnessed a number of novel approaches to manipulate the host's immune system to eliminate tumor cells. However, tumors displaying a "cold" immunogenic signature, characterized by the absence of infiltrating immune cells are often resistant to immune checkpoint inhibitors, targeting the PD-1 and CTLA-4 axes. Turning "cold" tumors "hot" by priming a vigorous cellular immune response would likely synergize with immune checkpoint inhibitors to be produce durable responses. The present invention is motivated by the lack of effective treatment options for metastatic tumors refractory to the current standard of care. It describes methods for synthesizing novel immunogenic complexes (microbial mimetics) designed to prevent or treat metastatic cancer, by harnessing the immune system's natural ability to eliminate microbial infected cells, which harbor the antigenic targets of activated T cells. In the context of microbial mimetics (MM), either tumor-specific or tumor-associated antigens may be referred to as "antigenic cargo" or "antigenic targets".

SUMMARY OF THE INVENTION

Disclosed herein are microbial mimetics (immunogenic compositions) designed to elicit an immune response against cancer cells by simulating an infection with microbes composed largely of tumor-associated or tumor-specific antigens. The microbial mimetics (MM) are comprised of peptide antigens and immune activating molecular motifs, which exhibit unique physical and biochemical properties, such as size tunability and enhanced immunogenicity. In part, enhanced immunogenicity arises from the utilization of a novel formulation and peptide design motif, which form stable MM complexes with multiple immune stimulatory molecules. The MM are comprised of combinations of lipopeptides, stabilizing amino acid linker sequences covalently bound to amino acid sequences with shared sequence homology to tumor antigens, and immunogenic DNA and RNA sequences, which are ionically attracted to the amino acid linker sequence (FIG. 1). The MM are designed to trigger a cellular immune response against tumor cells by inducing the release of antitumoral cytokines by immune cells and stimulating dendritic cells to activate T cells capable of targeting tumor cells, which express tumor-specific and/or tumor-associated antigens.

General Concept of MM

The MM are designed to be appear to the immune system as viral and bacterial sized particles loaded with tumor antigens and multiple immune-potentiating molecular motifs, thereby eliciting an immune response against tumor cells. In simplified language, the immune system sees as an assault by microbes comprised largely of tumor antigens, and cells harboring such antigens are viewed as the immune system as infected by microbes and become casualties in the subsequent immune response. MM can be readily modified to treat various forms of cancer by modifying the antigenic cargo, and can thus serve as a versatile immunogenic platform.

Advantages of MM Vs. Recombinant Vectors

Importantly, compared to recombinant viruses or bacteria expressing tumor antigens, which are largely composed of viral or bacterial antigens, the disclosed MM contain a very high tumor antigen content, exceeding 30% in all embodiments and comprising a majority of antigen content in other embodiments. This is advantageous compared to viral or bacterial vectors as the immune response is more focused toward activating and expanding tumor-specific T cells. As viruses and bacteria present the immune system with numerous foreign antigens, they are readily capable of expanding and activating T cells specific for viral or bacterial antigens. Furthermore, viral and bacterial antigens typically provide a stronger antigenic stimulus for T cell activation, and therefore induce more rapid expansion of T cells. Due to exponential outgrowth, the T cells which expand most rapidly become the dominant immune responders. For instance, during an acute viral infection, T cells can double every two hours with a potent stimulus. Compared to T cells which double every six hours due to a weaker stimulus, the 3× shorter doubling time, implies a 256-fold outgrowth in 24 hours. The disclosed MM which employ a higher tumor antigen content therefore enjoy the advantage of providing an immune stimulus, which is more focused toward expanding antitumoral T cells, rather than activating an immune response against the viral or bacterial vector.

DETAILED DESCRIPTION OF DISCLOSED EMBODIMENTS

Scope of Embodiments

Figure 1:
FIG. 1 is a generic representation of a single MM element containing a Pam(2)CSK4 moiety. The MM contains a peptide linker sequence comprised or arginine, histidine, and lysine residues, to which immunostimulatory DNA and RNA sequences ionically complex. The linker sequence is covalently linked to the antigen core peptide sequence via peptide bonds. The antigen core sequence is bound to the Pam(2)CSK4 molecule via a covelent peptide bond at the terminal lysine residue of Pam(2)CSK4.

Embodiments will be readily understood by the following detailed description in conjunction with the accompanying drawings and the appended claims. Embodiments are illustrated by way of example and not by way of limitation in the figures of the accompanying drawings. In the following detailed description, reference is made to the accompanying figures which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element. The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual, 2d ed.*, Cold Spring Harbor Laboratory Press, 1989; Sambrook et al., *Molecular Cloning: A Laboratory Manual, 3d ed.*, Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999. In addition, the materials, methods, and examples are illustrative only and not intended to be limiting.

Application of MM to Treat Multiple Tumor Types

The MM disclosed herein can also be used as an immunogenic platform or vehicle to treat other cancers by modifying the antigenic cargo. The modified MM could be used to treat, for example, solid tumors, such as sarcomas and carcinomas, including fibrosarcoma, myxosarcoma, liposarcoma, chondrosarcoma, osteogenic sarcoma and other sarcomas, synovioma, mesothelioma, Ewing's tumor, leiomyosarcoma, rhabdomyosarcoma, colon cancer (such as colon carcinoma), gastric cancer, (for example, gastric adenocarcinoma, such as intestinal type gastric adenocarcinoma and diffuse type gastric adenocarcinoma), lymphoid malignancy, pancreatic cancer, breast cancer (such as adenocarcinoma), lung cancers, gynecological cancers (such as cancers of the uterus (for example endometrial carcinoma), cervix (for example cervical carcinoma, pre-tumor cervical dysplasia), ovaries (for example, ovarian carcinoma, serous cystadenocarcinoma, mucinous cystadenocarcinoma, endometrioid tumors, celioblastoma, clear cell carcinoma, unclassified carcinoma, granulosa-thecal cell tumors, Sertoli-Leydig cell tumors, dysgerminoma, malignant teratoma), vulva (for example squamous cell carcinoma, intraepithelial carcinoma, adenocarcinoma, fibrosarcoma, melanoma), vagina (for example clear cell carcinoma, squamous cell carcinoma, botryoid sarcoma), embryonal rhabdomyosarcoma and fallopian tubules (for example carcinoma), prostate cancer, hepatocellular carcinoma, squamous cell carcinoma, basal cell carcinoma, adenocarcinoma, sweat gland carcinoma, medullary thyroid carcinoma, papillary thyroid carcinoma, anaplastic thyroid carcinoma, pheochromocytomas, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma) and skin cancer.

Design Synthesis and Characterization of MM

Selection of Antigenic Cargo

While many self-antigens are ubiquitously expressed in tissues vital to sustaining life, certain self-antigens, including calcitonin, thyroglobulin, prostate specific antigen, and melanoma differentiation antigens, among others, may be therapeutically targeted for cancers arising in organs expressing these antigens. For instance, medullary thyroid carcinomas express calcitonin, while papillary thyroid carcinomas express thyroglobulin. Melanomas express tyrosinase, gp100 and MART-1. Prostate carcinomas express prostate specific antigen. The antigenic cargo of MM may be modified to contain polypeptides with greater than 95% sequence homology to tissue-restricted antigens. Additionally, tumor cells harboring non-synonymous mutations are genetically distinct from the host. In such tumors, mutations in DNA may result in a single amino acid change from the native host sequence, creating tumor-specific antigens. Eliciting an immune response against cells expressing such non-self antigens would be therapeutically beneficial. The antigenic cargo of MM may be modified to contain such tumor-specific antigens. For each MM, the antigenic cargo is comprised of a polypeptide of 8 to 35 amino acids with greater than 95% sequence homology to a tumor-specific antigen or a tumor-associated antigen.

Selection of Unique Non-Homologous Core Sequences

To avoid using core sequences with a high potential to trigger autoimmunity due to off-target sequence homology, a subsequent filtering step is ideally employed for candidate polypeptide antigens. This filtering may be carried out as follows. Candidate peptide core sequences are first cross-referenced against the entire human genome using computational tools, such as the NIH's Basic Local Alignment Search Tool (BLAST). Specifically, the 9mers (continuous 9 amino acid segments) comprising each candidate peptide are separately screened against the entire genome. Any polypeptide with a 9mer which shares 7 or more amino acids (>77% sequence homology) is excluded. Of note, conservative amino acid substitutions, such as isoleucine (I) for leucine (V) are scored as 0.5 in the employed screening algorithm vs. 1.0 for perfectly matched amino acids.

Composition and Synthesis of MM

The MM are composed of multiple complexed elements, including:

1) Tumor-specific or tumor-associated antigenic cargo, i.e. a peptide sequence corresponding to at least one targeted tumor antigen, as described in the Selection of Antigenic Cargo subsection. The antigenic cargo is generally dissolved in a suitable buffer such as PBS, PBS with 0.1 to 2% acetic acid, and/or HEPES.

2) The novel peptide linker sequence containing arginine, histidine, and lysine residues (RRHRKRR) (SEQ. ID NO. 4), which is covalently coupled to the antigenic cargo at the amino terminus, the carboxy terminus or both termini. Critically, the novel linker sequence does not overlap with any known sequences in the human genome, based on BLAST analysis. The closest match is zinc finger protein 646, which bears 86% sequence homology. Together the antigenic cargo and the linker sequence(s) form the synthesized peptide.

3) An immunogenic, phosphorothioated DNA sequence, which is stably coupled to the synthesized peptide via ionic interactions between the linker sequence(s) and the phosphorothioate backbone. The DNA sequences employed are provided in Table 1. The use of such immunogenic DNA sequences as standalone agents was previously awarded patent protection to Isis Pharmaceuticals, Inc. in U.S. Pat. No. 6,727,230 titled "IMMUNE STIMULATION BY PHOSPHOROTHIOATE OLIGO-NUCLEOTIDE ANALOGS," which was filed on Sep. 11, 1996. The following DNA sequences were used for experiments: DNA4 (5'-TCGTCGGTTTCG-GCGCGCGCCG-3') and DNA10 (5'-TTCG-GCGCGCGCG:CGCGCGCCGTT-3').

4) A novel RNA sequence, termed RNA248, which is stably coupled to the synthesized peptide via ionic interactions between the linker sequences and phosphorothioate backbone of the RNA. RNA248 has the following sequence: 5'-guuggugguugugugagcgu-3', and is included in Table 1.

5) Optionally, a lipopeptide, such as Pam(2)CSK4 (S-(2,3-dipalmitate-propyl)cysteine-serine-lysine-lysine-lysine-lysine) or Pam(3)CSK4 (N-palmitoyl-S-[2,3-bis(palmitoyloxy)propyl]cysteine-serine-lysine-lysine-lysine-lysine) may be covalently conjugated to the synthesized peptide at the amino terminus. For instance, one exemplary peptide with an N-terminal linker sequence, and SVYDFFVWL antigenic cargo would by synthesized as Pam(2)CSKKKKRRHRKRRSVYDFFVWL. Anothery exemplary peptide with a C-terminal linker sequence would be synthesized as Pam(2)CSKKKKSVYD-FFVWLRRHRKRR.

Figure 2:
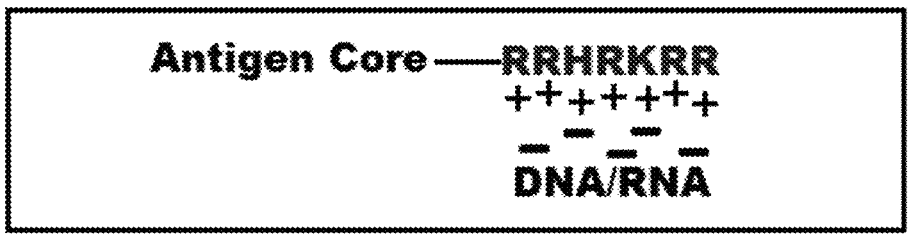
FIG. 2 is a generic representation of a single MM element without a Pam(2)CSK4 or Pam(3)CSK4 moiety.
Figure 3:
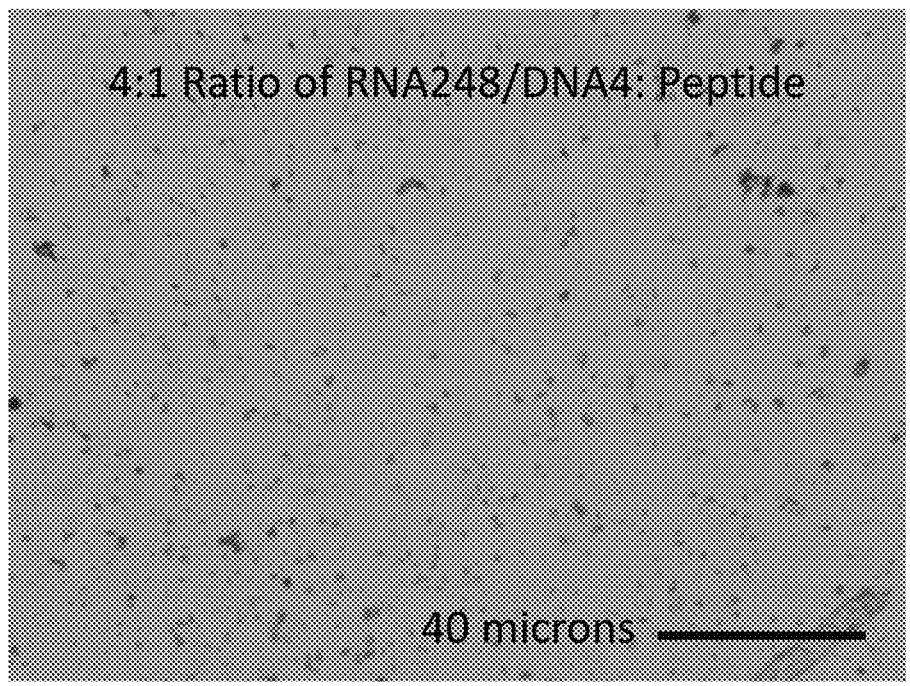
FIG. 3 is a microscope image of MM synthesized at a ratio of 4:1 RNA248/DNA4:peptide.
Figure 4:
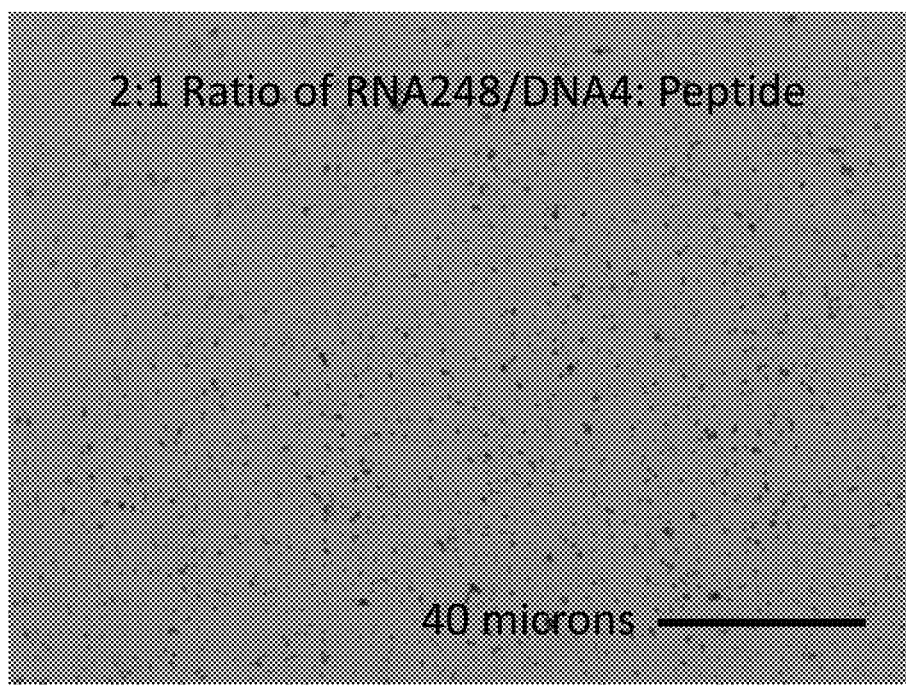
FIG. 4 is a microscope image of MM synthesized at a ratio of 2:1 RNA248/DNA4:peptide.
Figure 5:
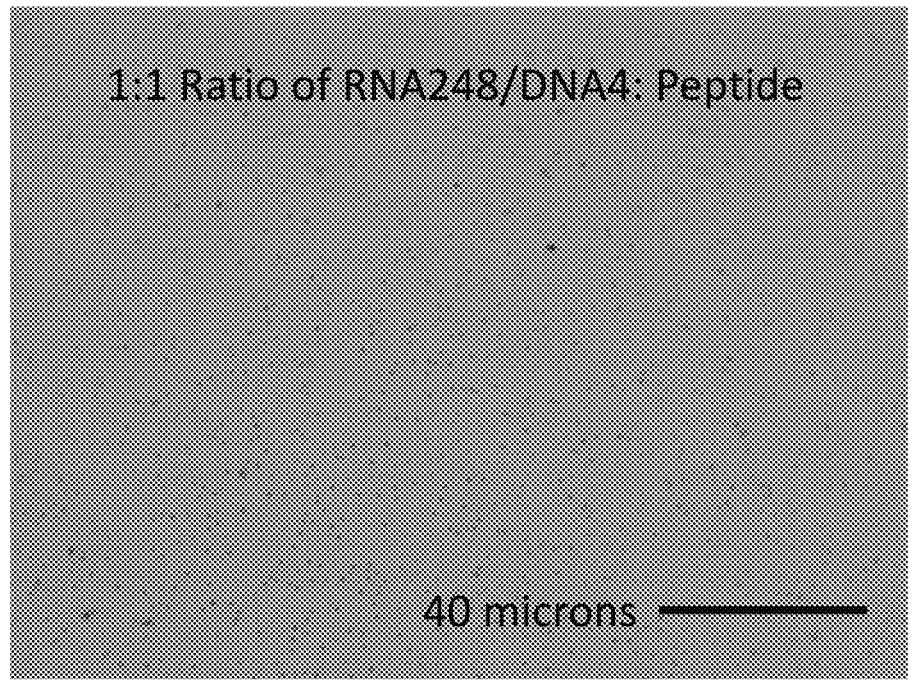
FIG. 5 is a microscope image of MM synthesized at a ratio of 1:1 RNA248/DNA4:peptide.
Figure 6:
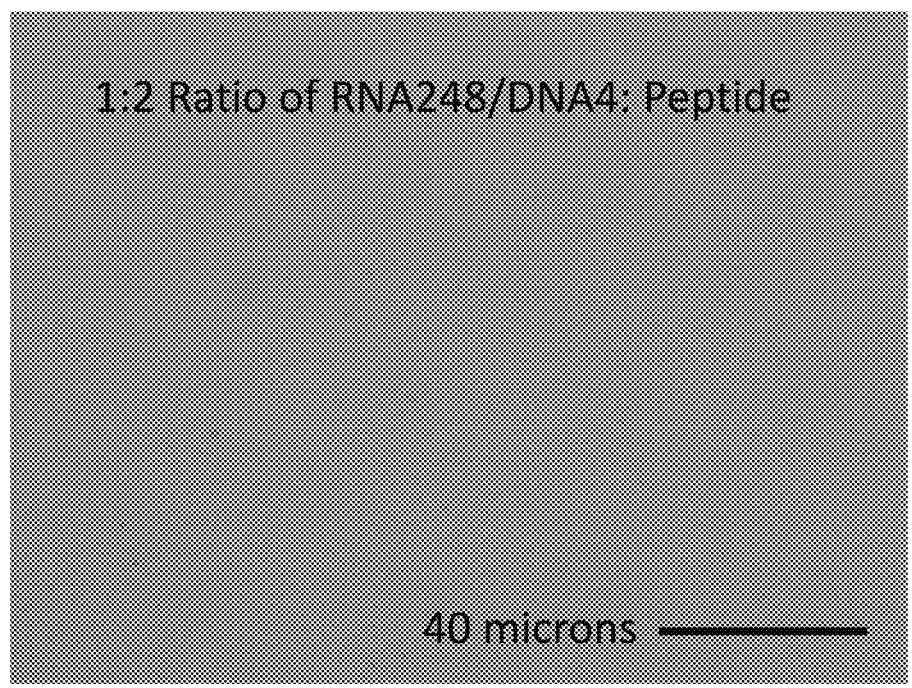
FIG. 6 is a microscope image of MM synthesized at a ratio of 1:2 RNA248/DNA4:peptide.

Generic illustrations of several embodiments are illustrated in FIG. 1 and FIG. 2. FIG. 1 shows an MM with a Pam(2)CSK4 lipopeptide attached at the amino terminus, whereas FIG. 2 shows an MM without a lipopeptide at the amino terminus.

TABLE 1

Immunostimulatory DNA and RNA Molecules

| SEQ. ID NO. | Name | Sequence |
|---|---|---|
| 1 | RNA248 | 5'-guuggugguugugugagcgu-3' |
| 2 | DNA4 | 5'-TCGTCGGTTTCGGCGCGCGCCG-3' |
| 3 | DNA10 | 5'-TTCGGCGCGCGCGCGCGCGCCGTT-3' |

TABLE 2

Peptide Sequences Used for Experiments

| SEQ. ID NO. | Name | Sequence |
|---|---|---|
| 4 | CAL2 | RRHRKRRLSTCMLGTYTQDFNKFHTFPQTAI |
| 5 | MEL2 | SVYDFFVWLRRHRKRR |
| 6 | MEL4 | Pam(2)CSKKKKSVYDFFVWLRRHRKRR |
| 7 | Linker Sequence | RRHRKRR |
| 8 | Trp2 | SVYDFFVWL |

Generic Method for Synthesis of MM

While a variety of synthesis methods may be employed, which are well known to those in the art, the following synthesis protocol is outlined for the purpose of showing one method by which MM may be synthesized. This exemplary MM contains a partial polypeptide sequence of human calcitonin as antigenic cargo.

Example 1

Formation of Microbial Mimetics in Solution

MM are readily formed by mixing stock solutions of the synthesized peptides and the stimulatory RNA and DNA sequences. In one embodiment, RNA248 and DNA4 are separately dissolved in PBS at a concentration of 2 mg/mL forming clear solutions. Then the RNA248 and DNA4 solutions (1 mL of each) are mixed together at equal volumes to form a clear solution with RNA248 and DNA4 at concentrations of 1 mg/mL with a volume of 2 mL. This solution is referred to as "RNA248/DNA4". Next, a synthesized peptide such as SEQ ID NO. 4 containing the (LSTC-MLGTYTQDFNKFHTFPQTAI) calcitonin core sequence is dissolved in PBS at a concentration of 2 mg/mL forming a clear solution with a volume of 2 mL. Then the synthesized peptide solution is slowly titrated into the RNA248/DNA4 solution in 100 µL increments. In this manner, the total volume of the synthesized peptide, hence the ratio of peptide to RNA248/DNA4 can be readily manipulated. Upon adding increasing amounts of the peptide, the initially clear solution becomes progressively cloudier. In other embodiments, RNA248/DNA4 may be slowly titrated into a synthesized peptide solution. The observation that the initially clear solution becomes increasingly opaque upon mixing inspired subsequent experiments to characterize the MM complexes, which spontaneously form upon mixing. As described below, it was determined that the complexes are quite stable and that their size can be readily varied by changing the ratio of RNA248/DNA4 to peptide.

Example 2

Size Tunability of MM Complexes

It is well known to those in the art that both the size and surface charge of particles can have a profound impact on cellular uptake. For example, experiments have shown that cellular uptake of particles is greatly enhanced when particles display a positive surface charge, and that DCs preferentially uptake particles with diameters below 500 nm and that particles with diameters below 100 nm bearing negative charge may be selectively internalized by dendritic cells. Of note, most microbes (bacterial and viruses) range in size from 50 nm to 10 microns, so the capacity to engineer particles to have these dimensions and the ability to readily tailor surface charge may be advantageous for stimulating an immune response. Importantly, both the size and charge of MM can be readily tuned by simple changing the ratio of RNA248/DNA4 to the synthesized polypeptide.

As a simple method to characterize the influence of mixing ratio on MM particle size, stock solutions of RNA248/DNA4 and peptide (SEQ ID NO. 4) were mixed at ratios of 4:1, 2:1, 1:1 and 1:2 and vigorously vortexed. Then a 10 µL droplet of each solution was placed on a microscope slide and allowed to dry. The images of each dried droplet at 40× are shown in FIG. 3, FIG. 4, FIG. 5 and FIG. 6, respectively. At high RNA248/DNA4 concentrations (4:1, FIG. 3), large clearly visible particulates formed which had a median diameter of ~10 µm. As the amount of peptide increases, the MM particles decreased in diameter and form relatively monodisperse ~2 µm rounded particulates when mixed at a 1:1 ratio. As the peptide concentration increases, the particles decrease in size to the point where they can no longer be resolved by the microscope.

Figure 7:
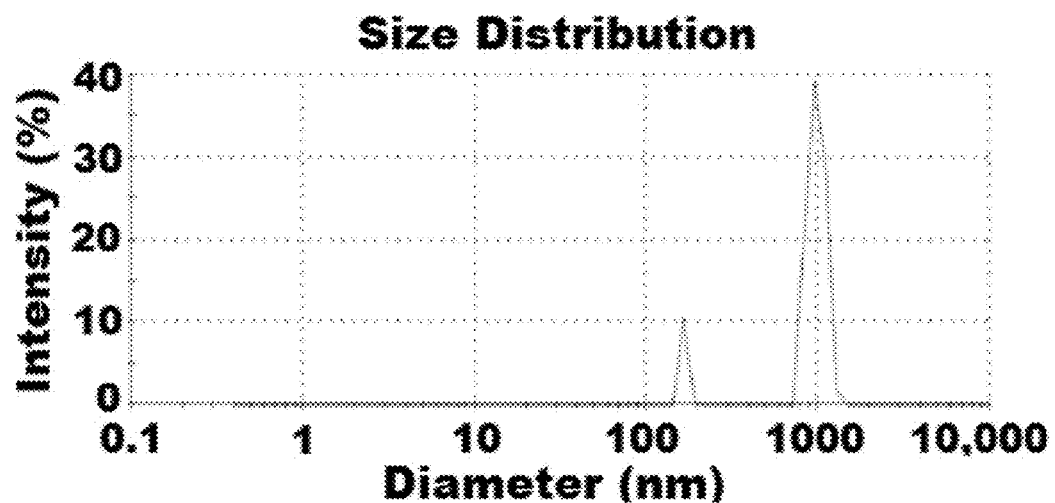
FIG. 7 is an image generated using a Malvern dynamic light scatter particle size analyzer, which shows the size distribution of MM when synthesized by mixing SEQ. ID NO. 4 (1 mg/mL) and DNA4/RNA248 (0.5 mg/mL for each nucleotide, 1 mg/ml total concentration) at a 1:1 ratio. At these concentrations particles range in size from 150 nm to 2 microns.
Figure 8:
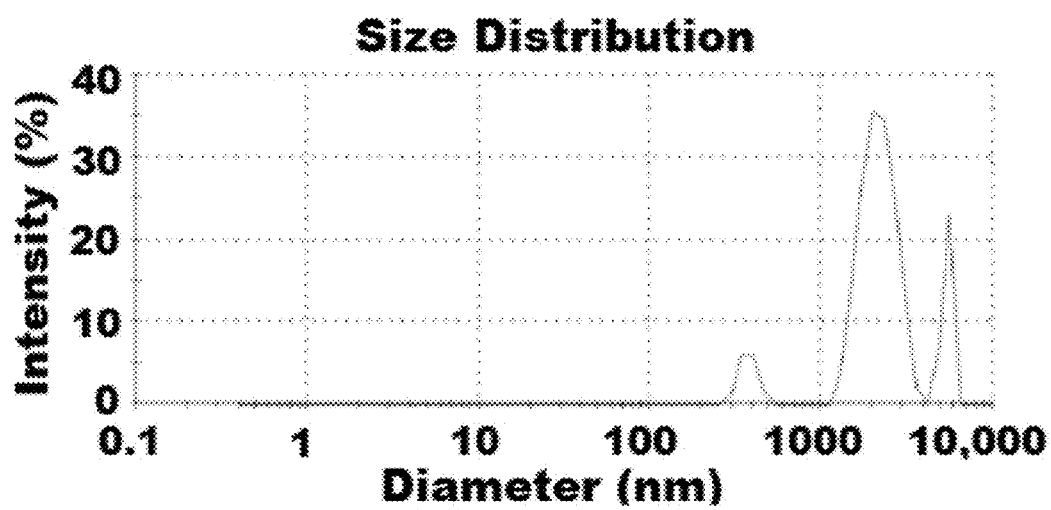
FIG. 8 is an image generated using a Malvern dynamic light scatter particle size analyzer, which shows the size distribution of MM when synthesized by mixing SEQ. ID NO. 4 (0.5 mg/mL) and DNA4/RNA248 (0.5 mg/mL for each nucleotide, 1.0 mg/ml total concentration) at a 1:1 ratio. At these concentrations particles range in size from 300 nm to 7 microns.

To characterize MM particles in this size range, solutions were characterized using Malvern Instruments DLS Particle Sizer. This method of particle sizing is also advantageous, as it can measure MM in solution. Experiments were run at various concentrations and representative results are provided for solutions mixed at RNA248/DNA4:peptide ratios of 1:2 (FIG. 7) and 2:1 (FIG. 8). At the 1:2 ratio, two populations of MM found with mean sizes of 150 nm 1000 nm. It not escaped the inventor's notice that these MM conveniently have sizes characteristic of viruses, such as HIV (150 nm) and small bacteria such as *E. Coli* (1000 nm). The size tunability of MM is a unique property, which permits MM to more faithfully replicate a true microbial infection, despite using a fully synthetic formulation.

To further evaluate the size tunability of MM for different peptide formulations, MEL2 (SEQ. ID NO. 5) and MEL4 (SEQ. ID NO. 6) were mixed with RNA248 at various concentrations. The results are provided in FIGS. 17 and 18. Mean particle diameter was measured using a Malvern particle size analyzer.

Figure 17:
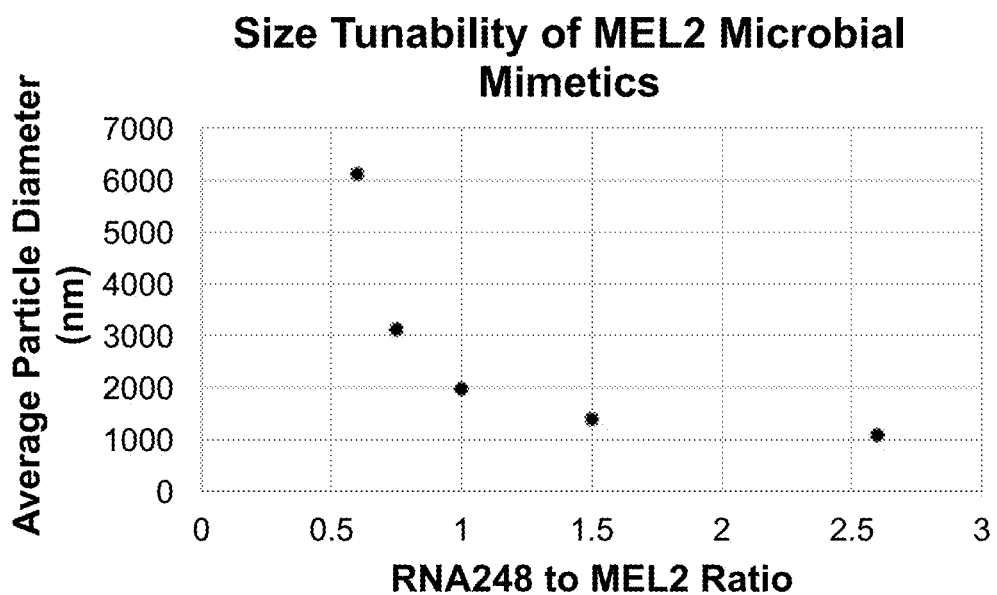
FIG. 17 is a plot demonstrating that the mean diameter of MM can be tuned by varying the ratio of RNA248 to MEL2 (SVYDFFVWLRRHRKRR). Both RNA248 and MEL2 were initially mixed at stock concentrations of 1 mg/mL and then MEL2 was titrated into 1 mL of RNA248 in 100 uL increments to produce solutions with the indicated ratios. As the concentration of MEL2 increases, the mean particle diameter decreases. Particle diameter was measured using a Malvern dynamic light scattering particle size analyzer.
Figure 18:
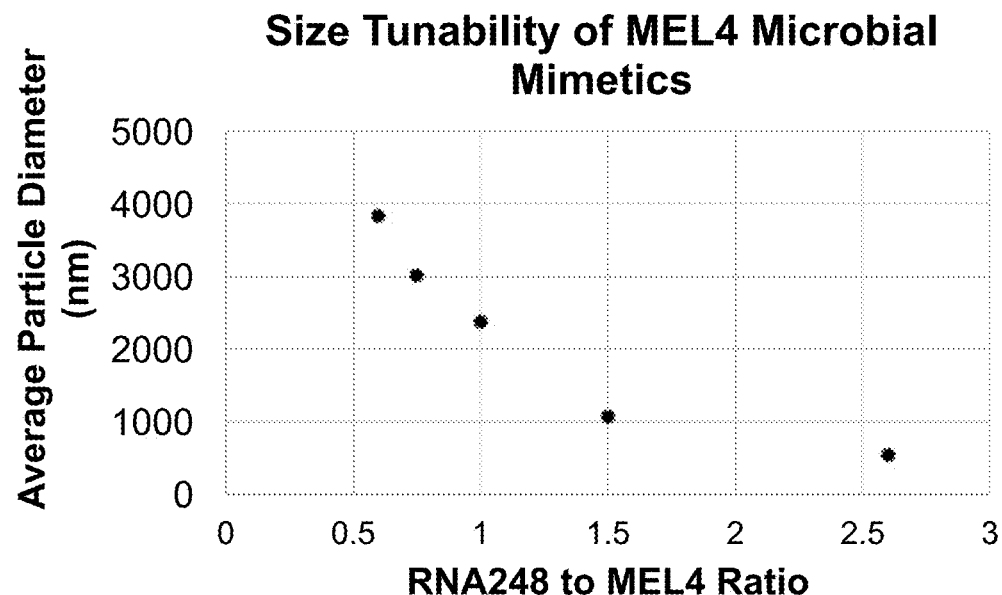
FIG. 18 is a plot demonstrating the mean diameter of MM can be tuned by varying the ratio of RNA248 to MEL4 (Pam(2)CSKKKKSVYDFFVWLRRHRKRR). Both RNA248 and MEL4 were initially mixed at stock concentrations of 1 mg/mL and then MEL4 was titrated into 1 mL of RNA248 in 100 uL increments to produce solutions with the indicated ratios. As the concentration of MEL4 increases, the mean particle diameter decreases in size from roughly four microns down to ~700 nm.

In general, the diameter of MM must be determined empirically for each polypeptide/RNA248/DNA4 combination as a function of concentration. However, there is a consistent trend of decreasing average particle diameter with increasing peptide concentration in the concentration ranges measured. FIG. 17 is a plot demonstrating that the mean diameter of MM can be tuned by varying the ratio of RNA248 to MEL2 (SVYDFFVWLRRHRKRR). Both RNA248 and MEL2 were initially mixed at stock concentrations of 1 mg/mL and then MEL2 was titrated into 1 mL of RNA248 in 100 uL increments to produce solutions with the indicated ratios. As the concentration of MEL2 increases, the mean particle diameter decreases. FIG. 18 is a plot demonstrating the mean diameter of MM can be tuned by varying the ratio of RNA248 to MEL4 (Pam(2)CSKK-KKSVYDFFVWLRRHRKRR). Both RNA248 and MEL4 were initially mixed at stock concentrations of 1 mg/mL and then MEL4 was titrated into 1 mL of RNA248 in 100 uL increments to produce solutions with the indicated ratios. As the concentration of MEL4 increases, the mean particle diameter decreases in size from roughly four microns down to ~700 nm.

Example 3

Characterization of MM Complex Stability

The complexation of immune stimulatory particles and antigenic cargo is known to be incredibly important for immunogenicity. It is known to those in the art that this can have a profound effect on cellular trafficking. The complexation explains, in part, why localized viral or bacterial infections which destroy tissue do not typically provoke autoimmune disease. Under inflammatory circumstances caused by bacterial infection, antigens are released from dying cells and there is an abundance of immune-stimulatory bacterial motifs, which may be simultaneously ingested by activated dendritic cells. However, the simultaneous presentation of self-antigens and bacterial "danger signals" does not typically produce autoimmune disease.

Indeed, recent studies have shown that dendritic cells are much more responsive to antigenic cargo when it is complexed to immune-stimulatory molecules. The recently discovered etiology of psoriasis is a prime example. When skin cells die, possibly due to infection, the cationic antimicrobial self-protein, LL37, becomes complexed to DNA, which is normally rapidly degraded by DNAases. The complexation of peptide plus immune-stimulatory DNA is able to trigger autoimmune disease. Thus, it is known that complexation of antigenic cargo with immune-stimulatory motifs is critical to triggering an immune response against self-antigens, and that such immune complexes can overcome both central and peripheral tolerance mechanisms.

Figure 9:
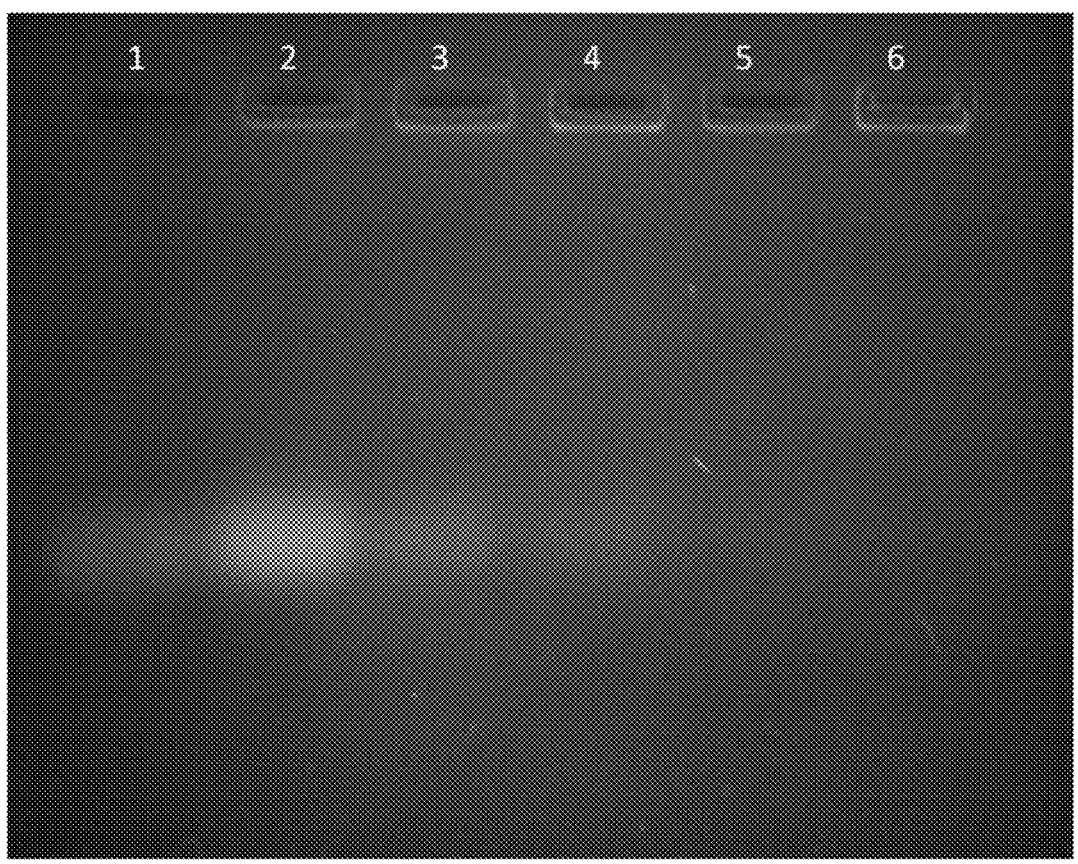
FIG. 9 is an image generated from a gel electrophoresis experiment (20 V/cm), whereby SEQ. ID NO. 4 (1 mg/mL) was mixed with DNA4/RNA248 (1 mg/mL) at ratios of 1:4 (Lane #2), 1:2 (Lane #3), 1:1 (Lane #4), 2:1 (Lane #5), and 4:1 (Lane #6) SEQ. ID NO. 4 to DNA4/RNA248. For reference, only DNA4/RNA248 was placed in Lane #1. The DNA4/RNA248 mixture travels in the gel away from the negative electrode (top) due its inherent negative charge. Notably, no nucleotide bands are seen in Lane #5 and Lane #6, which contain the highest concentrations of peptide. This indicates that at these peptide ratios, the DNA4/RNA248 are fully neutralized and remain stably complexed to the peptides.
Figure 10:
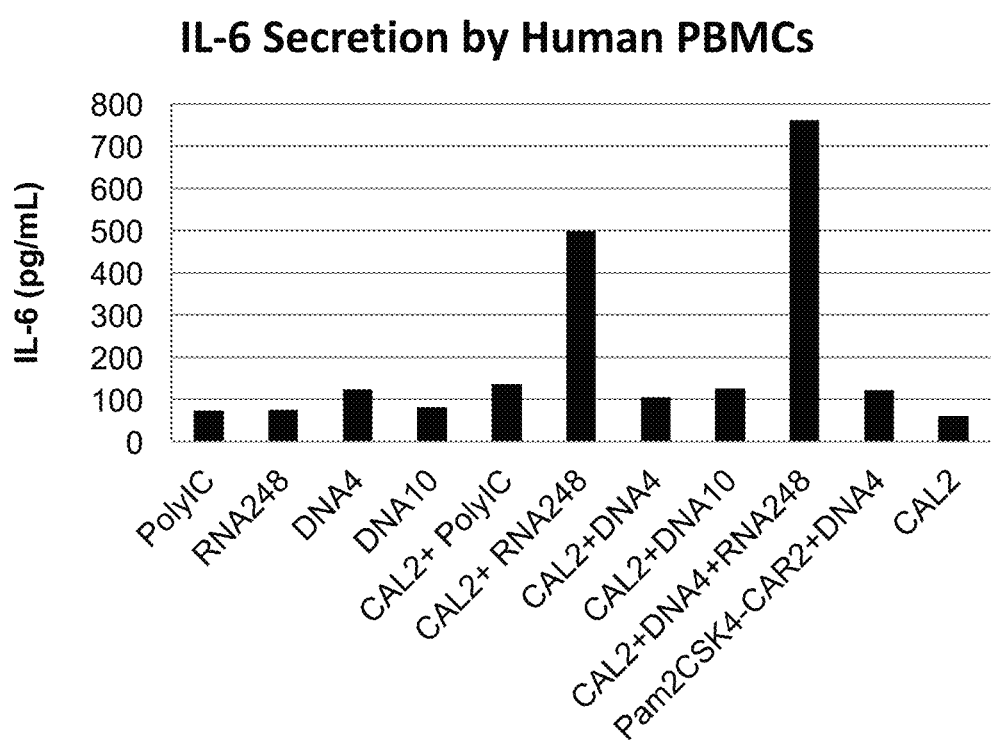
FIG. 10 is bar graph showing the induced secretion of IL-6 by PBMCs exposed to PolyIC, RNA248, DNA4, DNA10, PolyIC complexed with SEQ. ID NO. 4 (CAL2), RNA248 complexed with SEQ. ID NO. 4, DNA4 complexed with SEQ. ID NO. 4, DNA10 complexed with SEQ. ID NO. 4, DNA4 and RNA248 complexed with SEQ. ID NO. 4, Pam(2)CSK4-conjugated SEQ. ID NO. 4 complexed with DNA4 and SEQ. ID NO. 4 alone. Each well contained ~300,000 fresh PBMCs in a total volume of 100 μL of RPMI medium. Solutions of SEQ. ID NO. 4, PolyIC, DNA4, DNA10, Pam(2)CSK4-conjugated SEQ. ID NO. 4 were all pre-mixed to concentrations of 50 ug/mL (for each peptide reagent) and then added to wells in volumes of 100 uL, such that each well contained a 200 uL volume of PBMCs and reagents. Wells were run in triplicate and the mean value is indicated. The standard of deviation did not exceed 18% for all experiments.
Figure 11:
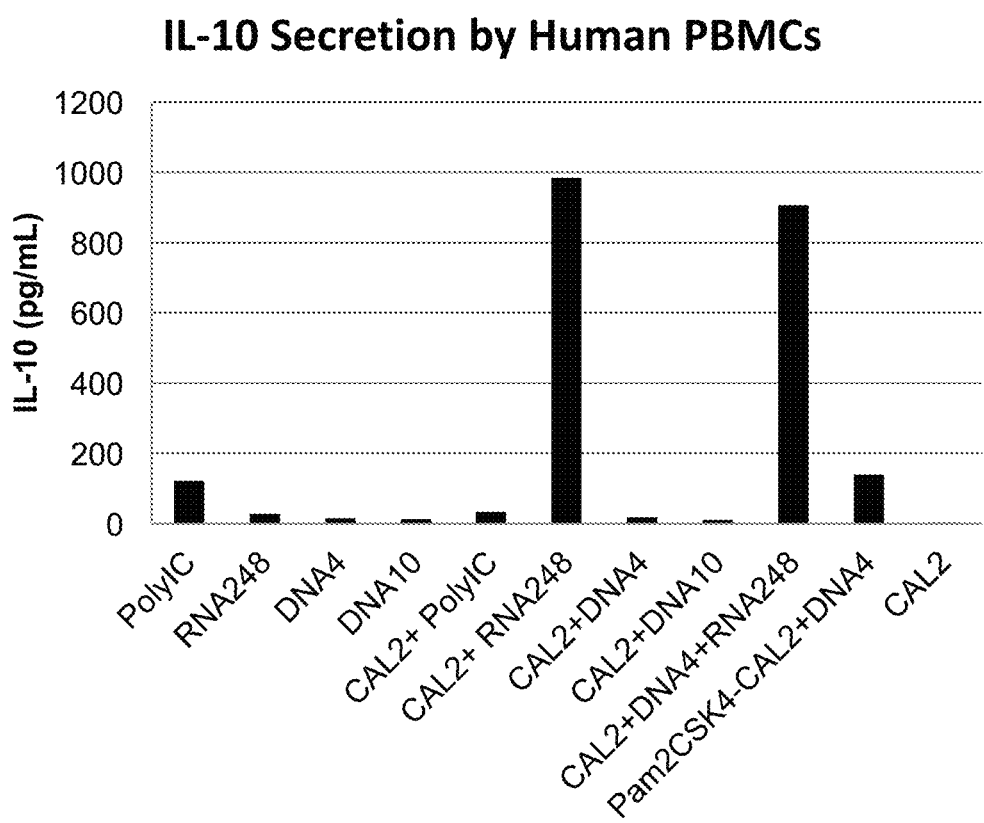
FIG. 11 is bar graph showing the induced secretion of IL-10 by PBMCs exposed to PolyIC, RNA248, DNA4, DNA10, PolyIC complexed with SEQ. ID NO. 4 (CAL2), RNA248 complexed with SEQ. ID NO. 4, DNA4 complexed with SEQ. ID NO. 4, DNA10 complexed with SEQ. ID NO. 4, DNA4 and RNA248 complexed with SEQ. ID NO. 4, Pam(2)CSK4-conjugated SEQ. ID NO. 4 complexed with DNA4 and SEQ. ID NO. 4 alone. Each well contained ~300,000 fresh PBMCs in a total volume of 100 μL of RPMI medium. Solutions of SEQ. ID NO. 4, PolyIC, DNA4, DNA10, Pam(2)CSK4-conjugated SEQ. ID NO. 4 were all pre-mixed to concentrations of 50 ug/mL (for each peptide reagent) and then added to wells in volumes of 100 uL, such that each well contained a 200 uL volume of PBMCs and reagents. Wells were run in triplicate and the mean value is indicated. The standard of deviation did not exceed 22% for all experiments.
Figure 12:
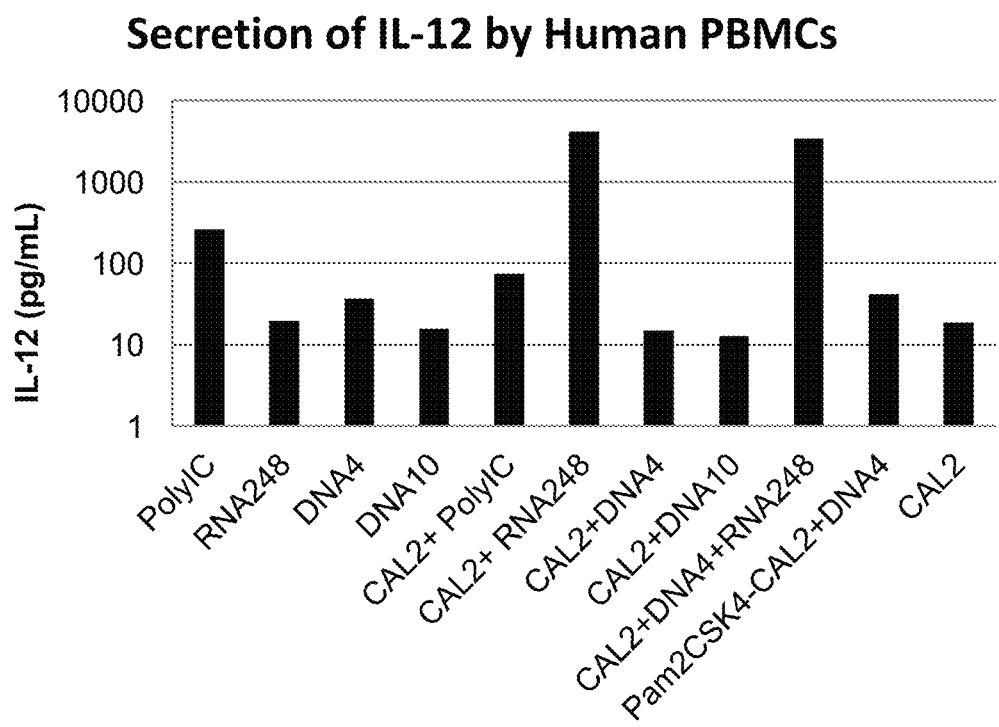
FIG. 12 is a bar graph showing the induced secretion of IL-12 by PBMCs exposed to PolyIC, RNA248, DNA4, DNA10, PolyIC complexed with SEQ. ID NO. 4 (CAL2), RNA248 complexed with SEQ. ID NO. 4, DNA4 complexed with SEQ. ID NO. 4, DNA10 complexed with SEQ. ID NO. 4, DNA4 and RNA248 complexed with SEQ. ID NO. 4, Pam(2)CSK4-conjugated SEQ. ID NO. 4 complexed with DNA4 and SEQ. ID NO. 4 alone. Each well contained ~300,000 fresh PBMCs in a total volume of 100 μL of RPMI medium. Solutions of SEQ. ID NO. 4, PolyIC, DNA4, DNA10, Pam(2)CSK4-conjugated SEQ. ID NO. 4 were all pre-mixed to concentrations of 50 ug/mL (for each peptide reagent) and then added to wells in volumes of 100 uL, such that each well contained a 200 uL volume of PBMCs and reagents. Wells were run in triplicate and the mean value is indicated. The standard of deviation did not exceed 17% for all experiments.
Figure 13:
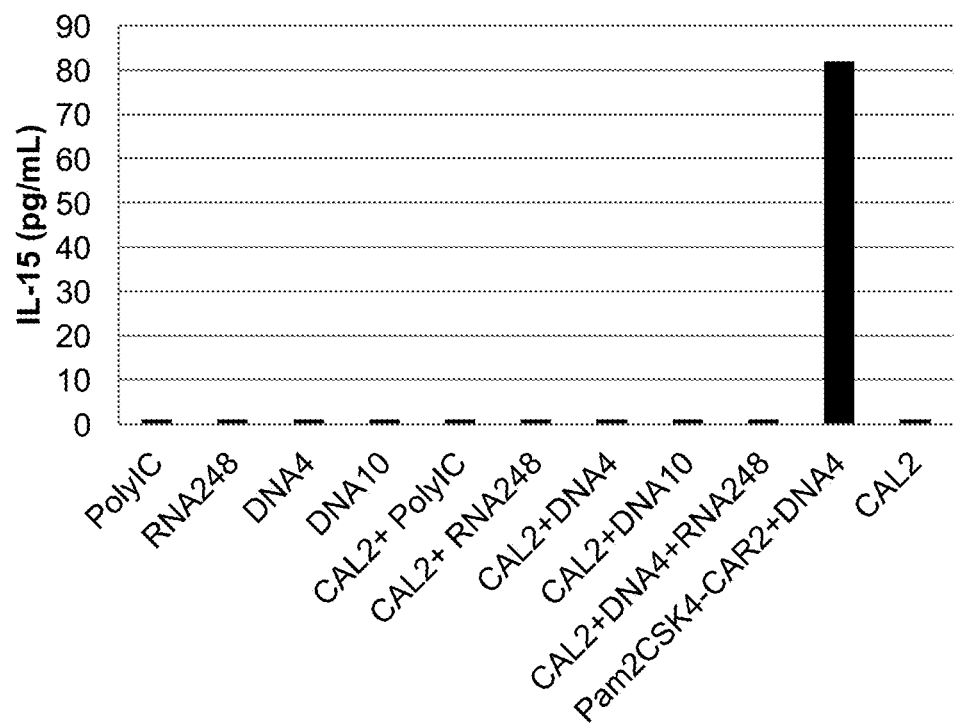
FIG. 13 is a bar graph showing the induced secretion of IL-15 by PBMCs exposed to PolyIC, RNA248, DNA4, DNA10, PolyIC complexed with SEQ. ID NO. 4 (CAL2), RNA248 complexed with SEQ. ID NO. 4, DNA4 complexed with SEQ. ID NO. 4, DNA10 complexed with SEQ. ID NO. 4, DNA4 and RNA248 complexed with SEQ. ID NO. 4, Pam(2)CSK4-conjugated SEQ. ID NO. 4 complexed with DNA4 and SEQ. ID NO. 4 alone. Each well contained ~300,000 fresh PBMCs in a total volume of 100 μL of RPMI medium. Solutions of SEQ. ID NO. 4, PolyIC, DNA4, DNA10, Pam(2)CSK4-conjugated SEQ. ID NO. 4 were all pre-mixed to concentrations of 50 ug/mL (for each peptide reagent) and then added to wells in volumes of 100 uL, such that each well contained a 200 uL volume of PBMCs and reagents. Wells were run in triplicate and the mean value is indicated. The standard of deviation did not exceed 25% for all experiments.
Figure 14:
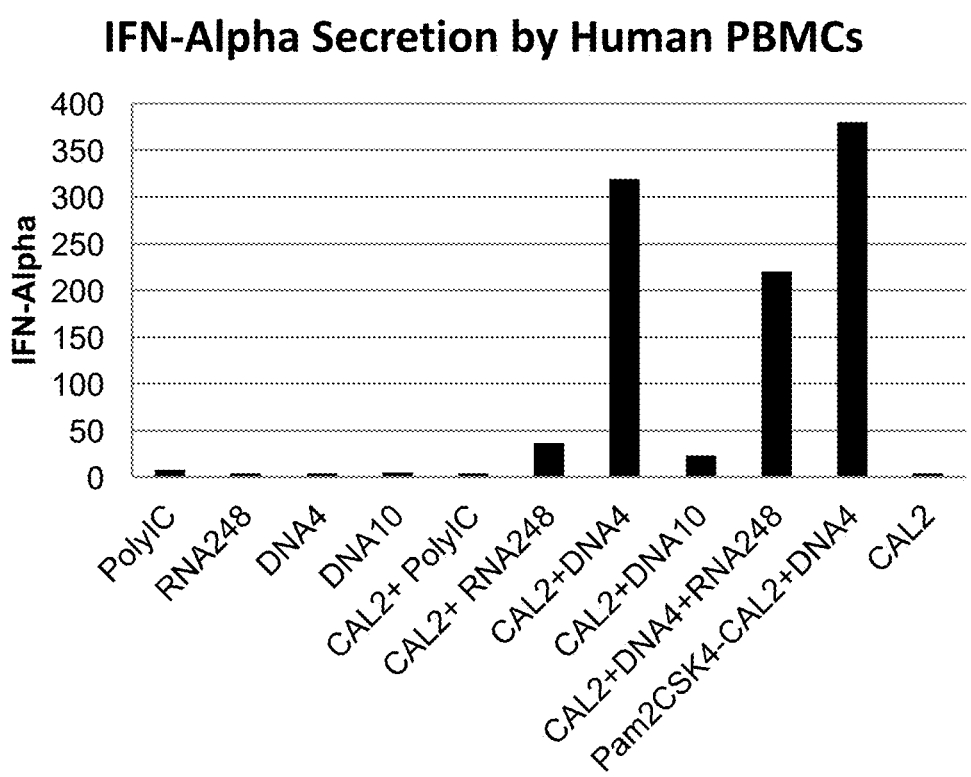
FIG. 14 is a bar graph showing the induced secretion of IFN-α by PBMCs exposed to PolyIC, RNA248, DNA4, DNA10, PolyIC complexed with SEQ. ID NO. 4 (CAL2), RNA248 complexed with SEQ. ID NO. 4, DNA4 complexed with SEQ. ID NO. 4, DNA10 complexed with SEQ. ID NO. 4, DNA4 and RNA248 complexed with SEQ. ID NO. 4, Pam(2)CSK4-conjugated SEQ. ID NO. 4 complexed with DNA4 and SEQ. ID NO. 4 alone. Each well contained ~300,000 fresh PBMCs in a total volume of 100 μL of RPMI medium. Solutions of SEQ. ID NO. 4, PolyIC, DNA4, DNA10, Pam(2)CSK4-conjugated SEQ. ID NO. 4 were all pre-mixed to concentrations of 50 ug/mL (for each peptide reagent) and then added to wells in volumes of 100 uL, such that each well contained a 200 uL volume of PBMCs and reagents. Wells were run in triplicate and the mean value is indicated. The standard of deviation did not exceed 22% for all experiments.
Figure 15:
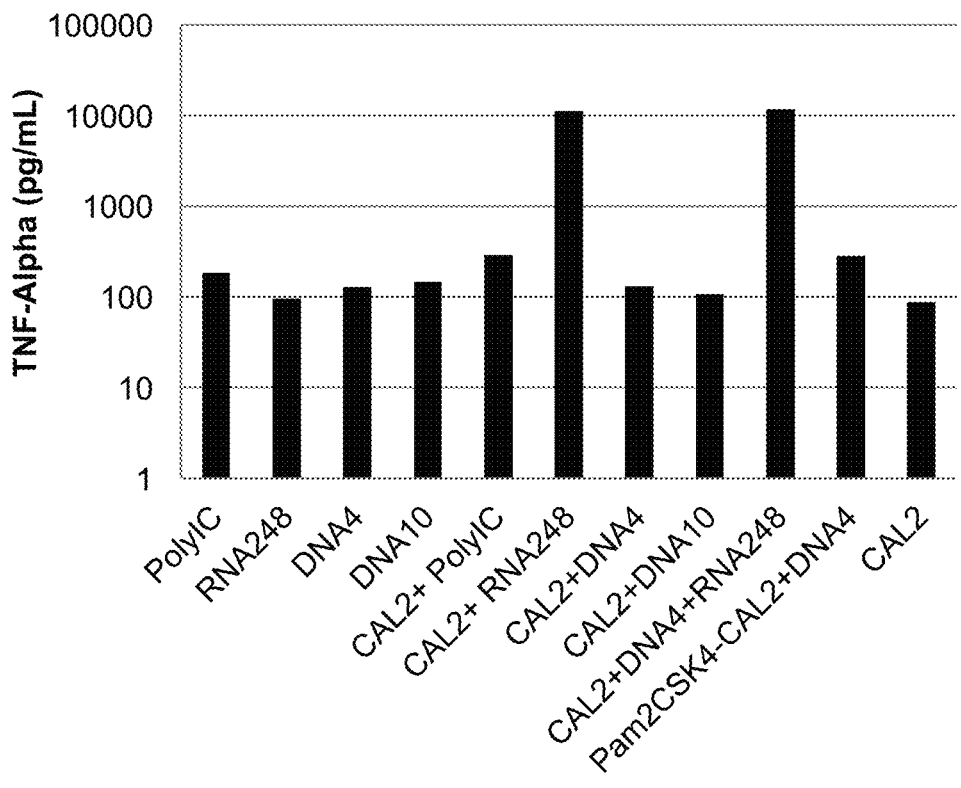
FIG. 15 is a bar graph showing the induced secretion of TNF-α by PBMCs exposed to PolyIC, RNA248, DNA4, DNA10, PolyIC complexed with SEQ. ID NO. 4 (CAL2), RNA248 complexed with SEQ. ID NO. 4, DNA4 complexed with SEQ. ID NO. 4, DNA10 complexed with SEQ. ID NO. 4, DNA4 and RNA248 complexed with SEQ. ID NO. 4, Pam(2)CSK4-conjugated SEQ. ID NO. 4 complexed with DNA4 and SEQ. ID NO. 4 alone. Each well contained ~300,000 fresh PBMCs in a total volume of 100 μL of RPMI medium. Solutions of SEQ. ID NO. 4, PolyIC, DNA4, DNA10, Pam(2)CSK4-conjugated SEQ. ID NO. 4 were all pre-mixed to concentrations of 50 ug/mL (for each peptide reagent) and then added to wells in volumes of 100 uL, such that each well contained a 200 uL volume of PBMCs and reagents. Wells were run in triplicate and the mean value is indicated. The standard of deviation did not exceed 27% for all experiments.
Figure 16:
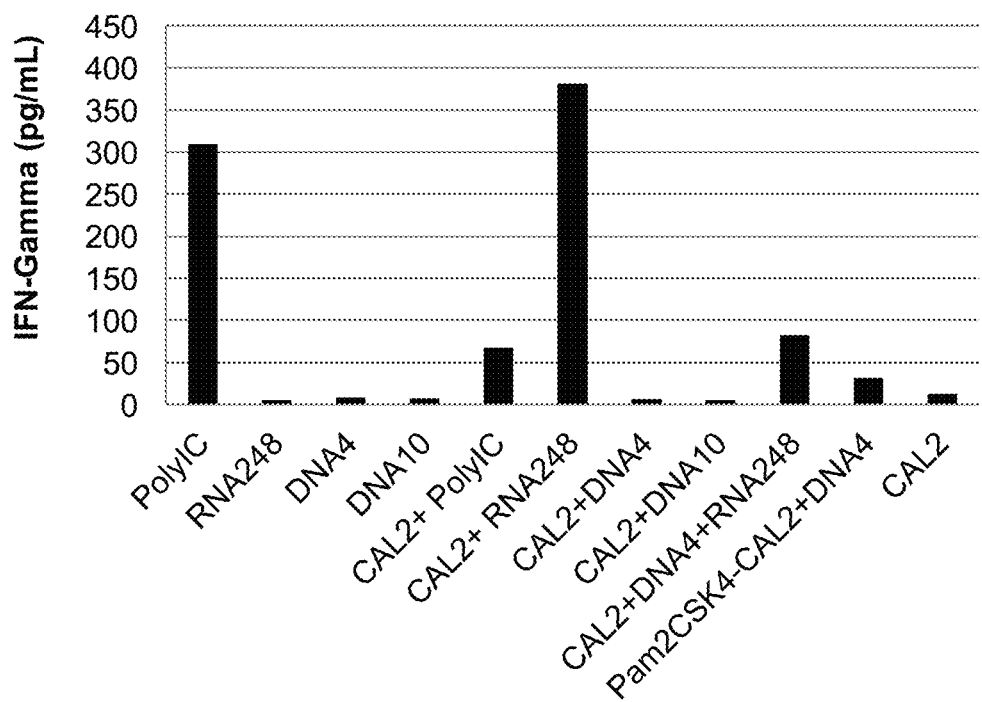
FIG. 16 is a bar graph showing the induced secretion of INF-γ by PBMCs exposed to PolyIC, RNA248, DNA4, DNA10, PolyIC complexed with SEQ. ID NO. 4 (CAL2), RNA248 complexed with SEQ. ID NO. 4, DNA4 complexed with SEQ. ID NO. 4, DNA10 complexed with SEQ. ID NO. 4, DNA4 and RNA248 complexed with SEQ. ID NO. 4, Pam(2)CSK4-conjugated SEQ. ID NO. 4 complexed with DNA4 and SEQ. ID NO. 4 alone. Each well contained ~300,000 fresh PBMCs in a total volume of 100 μL of RPMI medium. Solutions of SEQ. ID NO. 4, PolyIC, DNA4, DNA10, Pam(2)CSK4-conjugated SEQ. ID NO. 4 were all pre-mixed to concentrations of 50 ug/mL (for each peptide reagent) and then added to wells in volumes of 100 uL, such that each well contained a 200 uL volume of PBMCs and reagents. Wells were run in triplicate and the mean value is indicated. The standard of deviation did not exceed 14% for all experiments.

As previously descried, MM were observed to readily form complexes in solutions, and the size of the MM complexes could be readily tuned. Given the importance of forming stable complexes of antigenic cargo with immune-stimulatory molecules, the stability of MM was characterized using gel electrophoresis. MM were formed by mixing CAL2 (SEQ ID NO. 4) with DNA4/RNA48 at varying ratios. As indicated in FIG. 9, at peptide to DNA4/RNA248 ratios exceeding 2:1, no free DNA4/RNA248 could be visualized, indicating that all DNA4/RNA48 remained bound to the peptide, even in an electric field of 20 V/cm. Stable complexes were formed as indicated by the disappearance of free DNA4/RNA248 at sufficient peptide concentrations. Furthermore, the intensity of each band decreased as concentration of peptide increased. The presence of the linker sequence, RRHRKRR, was determined to be critical for stable complexation. Separately, solutions of MM were tested after sitting at room temperature for 2 weeks yielding nearly identical results.

Procurement of MM Sub-Components

The synthesized peptide may be readily manufactured as outlined in the Peptide Synthesis subsection. Conjugation is readily achieved using standard Fmoc chemistry. For the purposes of this invention, peptides were procured from a single commercial supplier (Lifetein, Hillsborough, N.J.). Peptides were shipped to the inventor in lyophilized form in 2 mL freezer vials, packed under non-reactive argon gas, and reconstituted in PBS or PBS+1% acetic acid at various stock concentrations in the range of 0.025 mg/mL to 2 mg/mL.

The stimulatory DNA and RNA sequences may be readily manufactured as outlined in the Nucleotide Synthesis subsection. Lyophilized DNA and RNA sequences were purchased commercially from AlphaDNA (Montreal, Canada) and Trilink Biotechnologies (San Diego, Calif.), respectively. Prior to synthesis, they were reconstituted in PBS at various concentrations in the range of 0.025 mg/mL to 2 mg/mL to form stock solutions for experiments.

Synthesis of Polypeptides

The polypeptides used in the disclosed immunogenic compositions can be made by any method available in the art with the applied and preferred method of using solid-phase polypeptide synthesis techniques familiar to those in the art, including Fmoc chemistry, or purification of polypeptides from recombinant prokaryotic or eukaryotic sources. Both Pam(2)CSK4 and Pam3CSK4 can be procured from multiple commercial suppliers, such as Torcris Bioscience, Lifetein, and Invivogen, as starter materials for synthesis of longer peptides, with either Pam(2)CSK4 or Pam3CSK4 located at the amino terminus.

Peptides for the disclosed immunogenic compositions may be produced, for example by chemical synthesis by any of a number of manual or automated methods of synthesis known in the art. In addition, polypeptides that form all or part of a hetero-bifunctional ligand can be produced synthetically. For example, solid phase polypeptide synthesis (SPPS) is carried out on a 0.25 millimole (mmole) scale using an Applied Biosystems Model 43 IA Peptide Synthesizer and using 9-fluorenylmethyloxycarbonyl (Fmoc) amino-terminus protection, coupling with dicyclohexylcarbodiimide/hydroxybenzotriazole or 2-(IH-benzo-triazol-1-yl)-1,1,3,3-tetramethyluroniumhexafluorophosphate/hydroxybenzotriazole (HBTU/HOBT) and using p-hydroxymethylphenoxymethylpolystyrene (HMP) or Sasrin resin for carboxyl-terminus acids or Rink amide resin for carboxyl-terminus amides. Fmoc-derivatized amino acids are prepared from the appropriate precursor amino acids by tritylation and triphenylmethanol in trifluoroacetic acid, followed by Fmocderivitization as described by Atherton et al. Solid Phase Peptide Synthesis, IRL Press: Oxford, 1989.

Synthesis of RNA and DNA Nucleotides and Antigens Encoded by RNA or DNA

Nucleic acid sequences encoding immuno-stimulatory RNA, DNA, or immunogenic polypeptides can be prepared by any suitable method including, for example, cloning of appropriate sequences or by direct chemical synthesis by methods such as the phosphotriester method of Narang et al, Meth. Enzymol. 68:90-99, 1979; the phosphodiester method of Brown et al, Meth. Enzymol. 68: 109-151, 1979; the diethylphosphoramidite method of Beaucage et al, Tetra. Lett. 22: 1859-1862, 1981; the solid phase phosphoramidite triester method described by Beaucage & Caruthers, Tetra. Letts. 22(20): 1859-1862, 1981, for example, using an automated synthesizer as described in, for example, Needham-VanDevanter et al., Nucl. Acids Res. 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template.

Applications of MM

The MM disclosed herein are useful for stimulating or eliciting a specific immune response in a human. In some embodiments, the immunogenic response is protective or provides protective immunity against cancer. The disclosed immunogenic compositions include one or more isolated polypeptides, such as a plurality, that, when administered to a subject, elicit an immune response to tumor-specific or tumor-associated antigens.

Therapeutic Formulations

The MM immunogenic compositions disclosed herein may be included in pharmaceutical compositions (including therapeutic and prophylactic formulations), and may be combined together with one or more pharmaceutically acceptable vehicles. Such pharmaceutical compositions can be administered to subjects by a variety of administration modes, including by intramuscular, subcutaneous, intravenous, intra-atrial, intra-articular, intraperitoneal, parenteral routes oral, rectal, intranasal, intrapulmonary, or transdermal delivery, or by topical delivery to other surfaces.

To formulate a pharmaceutical composition, the MM can be combined with various pharmaceutically acceptable additives, as well as a base or vehicle for dispersion of the immunogenic compositions. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, TWEEN® 80), solubility enhancing agents (for example, cyclodextrins and derivatives thereof), stabilizers (for example, serum albumin), and reducing agents (for example, glutathione) can be included.

When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The MM immunogenic composition can be dispersed in a base or vehicle, which can include a hydrophilic compound having a capacity to disperse the immunogenic composition, and any desired additives. The MM of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitanmonolaurate, and triethanolamineoleate. For solid compositions, conventional nontoxic pharmaceutically acceptable vehicles can be used which include, for example, pharmaceutical grades of mannitol, sorbitol, lactose, starch, magnesium stearate, sodium saccharin, talcum, cellulose, glucose, sucrose, magnesium carbonate, and the like.

Pharmaceutical compositions for administering the MM can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the immunogenic compositions can be brought about by including in the composition an agent which delays absorption, for example, monostearate salts and gelatin.

In certain embodiments, the MM immunogenic composition can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various immunogenic compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the immunogenic composition and/or other biologically active agent. Many methods for preparing such formulations are well known to those skilled in the art (see, for example, Sustained and Controlled Release Drug Delivery Systems, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble polypeptides (U.S. Pat. No. 4,675,189).

In additional to chemically-dependent time release formulation, the dose of the immunogenic composition and hence the amount of antigen encountered by dendritic cells can be controlled through dosing schedule and magnitude. For example, to mimic an acute viral infection, the immunogenic composition may be administered on a daily or hourly basis, starting at a small dose, an increasing the dose in a linear or exponential manner over the course of several hours or days until the maximum tolerable dose is reached.

The pharmaceutical compositions of the disclosure typically are sterile and stable under conditions of manufacture, storage and use. Sterile solutions can be prepared by incorporating the immunogenic compositions in the required amount in an appropriate solvent with one or a combination of ingredients enumerated herein, as required, followed by filtered sterilization. Generally, dispersions are prepared by incorporating the immunogenic composition and/or other biologically active agent into a sterile vehicle that contains a basic dispersion medium and the required other ingredients from those enumerated herein. In the case of sterile powders, methods of preparation include vacuum drying and freeze-drying which yields a powder of the immunogenic composition plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

Methods of Treatment

The MM disclosed herein can be used in methods of generating or eliciting an immune response, treating a subject with cancer and decreasing the growth rate of a tumor, as described below.

In several embodiments, the methods include administering to a subject with an effective amount, such as an immunologically effective dose, of one or more of the MM disclosed to generate an immune response. The methods can include selecting a subject in need of treatment, such as a subject that has, is suspected of having, or is predisposed to having cancer, for example a solid tumor. Also disclosed are methods for treating a subject having or suspected of having cancer. Such methods include selecting a subject having or suspected of having cancer, and administering to the subject a therapeutically effective amount of a disclosed MM immunogenic composition, thereby treating the subject.

An immune response is a response of a cell of the immune system, such as a B-cell, T-cell, macrophage or polymorphonucleocyte, to a stimulus. An immune response can include any cell of the body involved in a host defense response. An immune response includes, but is not limited to, an adaptive immune response or inflammation.

In exemplary applications, the immunogenic compositions are administered to a subject having a disease, such as cancer (for example, medullary thyroid carcinoma), in an amount sufficient to raise an immune response to cells expressing the antigens targeted by the immunogenic composition. Administration induces a sufficient immune response to slow the proliferation of such cells or to inhibit their growth, or to reduce a sign or a symptom of a tumor. Amounts effective for this use will depend upon the severity of the disease, the general state of the patient's health, and the robustness of the patient's immune system. In one example, a therapeutically effective amount of MM which provides either subjective relief of a symptom(s) or an objectively identifiable improvement as noted by the clinician or other qualified observer.

Typical subjects intended for treatment with the compositions and methods of the present disclosure include human patients. To identify patients for treatment, accepted methods are used to diagnose or stage suspected disease, such as medical imaging (CT, MRI, ultrasound, PET and/or X-rays), biopsies, histology and/or serum tumor biomarker measurements. These and other routine methods allow the clinician to select patients in need of therapy using the methods and pharmaceutical compositions of the disclosure. In accordance with these methods and principles, MM immunogenic compositions can be administered according to the teachings herein as an independent prophylaxis or treatment program, or as a follow-up, adjunct or coordinate treatment regimen to other treatments, including surgery, immunotherapy, hormone treatment, and the like.

The immunogenic compositions can be used in coordinate treatment protocols or combinatorial formulations. As an example, the immunogenic composition described herein, can be administered concurrently or sequentially with immune checkpoint inhibiting antibodies, which bind to PD-1, such as nivolumab and pembrolizumab or those which bind to CTLA-4, such as ipililumab.

The administration of the immunogenic compositions of the disclosure can be for either prophylactic or therapeutic purpose. When provided prophylactically, the immunogenic composition is provided in advance of any symptom. The prophylactic administration of the immunogenic composition serves to prevent or ameliorate any progression on the disease. When provided therapeutically, the immunogenic composition is provided at (or shortly after) the onset of a symptom of disease. For prophylactic and therapeutic purposes, the immunogenic compositions can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol) with exponentially increasing doses designed to mimic an acute viral infection. The therapeutically effective dosage of the MM can be provided as repeated doses within a prolonged prophylaxis or treatment regimen.

Determination of effective dosages in this context is typically based on animal model studies followed up by human clinical trials and is guided by administration protocols that optimize clinical outcomes. Suitable models in this regard include, for example, murine, rat, porcine, feline, non-human primate, and other accepted animal model subjects known in the art.

Upon administration of a MM immunogenic composition of the disclosure (for example, via injection, aerosol, oral, topical or other route), the immune system of the subject typically responds to the immunogenic composition by secreting cytokines, such as IFN-α, IL-12, TNF-α and inducing dendritic cells to activate naïve tumor-specific T cells. Such activated T cells may rapidly proliferate in number.

An immunologically effective dosage can be achieved by single or multiple administrations (including, for example, multiple administrations per day), daily, or weekly administrations. For each particular subject, specific dosage regimens can be evaluated and adjusted over time according to the individual need and professional judgment of the person administering or supervising the administration of the immunogenic composition. In other instances, the cellular immune response of T cells may be enumerated by ELISPOT assays or tetramer staining or tumor marker measurements or medical imaging. Decisions as to whether to administer booster inoculations and/or to change the amount of the composition administered to the individual can be at least partially based on T cell activation assays.

Dosage can be varied by the attending clinician to maintain a desired concentration. Higher or lower concentrations can be selected based on the mode of delivery. Dosage can also be adjusted based on the release rate of the administered formulation.

Kits are also envisioned. In one embodiment, these kits include a container or formulation that contains the materials for a pharmacist to generate MM from lyophilized products by simple mixing or titrating of ingredients. In one example, this component is formulated in a pharmaceutical preparation for delivery to a subject. The MM are optionally contained in a bulk dispensing container or unit or multi-unit dosage form. Optional dispensing means can be provided. Packaging materials optionally include a label or instruction indicating for what treatment purposes and/or in what manner the pharmaceutical agent packaged therewith can be used.

Reservation to Modify MM Composition for Personalized Cancer Therapy

Tumors arising from the same cell type in different patients invariably exhibit highly distinct molecular characteristics, relating to both underlying mutations and gene expression, which drive the tumor phenotype. To a lesser degree, tumors within the same patient can exhibit such diversity. Using established methods familiar to those in the art, such as whole exome sequencing, mRNA profiling or immunohistochemical staining, the unique genomic and proteomic expression profile of a patient's tumor specimen can be reliably ascertained. In this context, the MM solutions can be formulated, to include MM with various polypeptides. By design, this approach will permit tumor-specific or tumor-associated antigens to be targeted, while sparing the patient from any potential side effects related to vaccinating against antigens absent from the patient's tumor.

MM Delivery, Dosing and Scheduling

MM can be administered to the patient via intranodal, intradermal or intramuscular injections in multiple body locations. The total dose of MM can be varied. In general, the dose should range from 100 μg to 50 mg for each MM with doses tailored based on tolerability and dose-related immune responses. In particular, to mimic an acute viral infection, both simultaneous intramuscular and intradermal dosing schemes may be employed, whereby treatments are administered daily, and each is double of the previous day, such that there is exponential growth in the magnitude of the dose, up to the point where the maximum tolerable dose is reached. Intradermal administration is used to supply a steady dose of MM to the draining lymph nodes, whereby intramuscular administration, due to increased perfusion, is used to simulate a rapidly escalating infection, as simulated by the MM.

The ability to simulate an acute viral infection has proven to be an effective method for protective immunity. As a prime example, the YF-17D yellow fever vaccine, a live, attenuated virus often provides lifetime protection from yellow fever. YF-17D faithfully replicates a true acute viral infection and induces polyfunctional memory CD8+ T cell responses. Analysis has shown that viral load peaks approximately 7 days after vaccination and becomes undetectable ~14 days after the initial dose, as T cell response increases in magnitude, peaking around day 30. Furthermore, analysis has shown that T cell responses increase with magnitude of viral load (antigenic stimulus), up to a saturation point of approximately $10^3$ viral copies/mL. Thus, MM may be preferably employed in a dosing scheme, which faithfully replicates an acute viral infection, similar to YF-17D infection. Such a dosing scheme would ensure that antigenic stimulus rises as the number of activated T cells increase in magnitude, further priming an effective immune response without wasting antigenic stimuli too early in the priming process.

Application and Adaptation of Embodiments

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

Example 4

In Vitro Immunogenicity Studies of MM and Molecular Sub Units Comprising MM

A series of in vitro experiments was conducted to characterize the immune-stimulating properties of the MM and their sub-components. Human peripheral blood mononuclear cells (PBMCs) were exposed to a MM containing SEQ. ID NO. 4 and its individual molecular sub-components for 24 hours. For reference, the PBMCs were separately exposed to PolyIC. After this time, the induced secretion of following cytokines by PBMCs was measured: interleukin-6 (IL-6), interleukin-10 (IL-10), interleukin-12 (IL-12), interleukin-15 (IL-15), tumor necrosis factor alpha (TNF-alpha), interferon-alpha (IFN-alpha), and interferon-gamma (IFN-gamma). Experiments were conducted as follows. 150 mL of blood was supplied by a human volunteer and PBMCs were isolated by Ficoll-Paque gradient centrifugation immediately after venipuncture. PBMCs were incubated for 24 hours at 37° C./5% $CO_2$ in 96-well plates, with 300,000 PBMCs per well in a 200 μL medium containing 49% RPMI-1640/49% PBS/1% L-glutamine/1% penicillin-streptomycin and the components in Table 3 at a concentration of 25 μg/mL. All cytokines were measured in triplicate.

TABLE 3

MM and Molecular Components Used for In Vitro Studies

| Label | Description |
|---|---|
| PolyIC | Polyinosinic:polycytidylic acid |
| CAL2 | RRHRKRRLSTCMLGTYTQDFNKFHTFPQTAI |
| RNA248 | 5'-guugguggguugugugagcgu-3' |
| DNA4 | 5'-TCGTCGGTTTCGGCGCGCGCCG-3' |
| DNA10 | 5'-TTCGGCGCGCGCGCGCGCGCCGTT-3' |
| MM1 | CAL2 + DNA4 + RNA248 |
| MM2 | Pam(2)CSKKKKRRHRKRRLSTCMLGTYTQDFNKFHTFPQTAI + DNA4 |

After 24 hours, the supernatant from each well was isolated using centrifugation at 3000 g and immediately thereafter cytokines were measured using ELISA kits from Genway Biotech (San Diego, Calif.) and Origene (Rockville, Md.). Per ELISA kit instructions, 100 μL of supernatant was used for each readout. The results are provided in FIGS. 10-16, where the mean of each measurement is provided. (In no instance did the standard deviation exceed 30%.)

Enhanced and Synergistic Immunogenicity of MM

This dataset reveals that MM1 and MM2 are highly immunogenic, inducing the secretion of high-levels of IL-6, IL-10, IL-12, TNF-alpha, IFN-alpha and IFN-gamma. Notably, of all components tested only MM2 was able to induce secretion of IL-15. Importantly, the MM were able to induce higher levels of IL-12 and IFN-alpha than PolyIC. It is essential to note that on their own, RNA248, DNA4, and DNA10 induced minimal cytokine secretion, but there is a marked increase when complexed to the CAL2 peptide (RRHRKRRLSTCMLGTYTQDFNKFHTFPQTAI) containing the linker sequence (RRHRKRR) at the amino terminus. Thus the MM, by complexation with multiple immune-stimulating motifs, induce enhanced secretion of multiple cytokines in a synergistic manner. Indeed, the immunogenicity of the MM is much greater than the sum of its parts. As individual components, RNA248 and CAL2 potentiate very minimal cytokine secretion, which is close to or below the limit of detection. Furthermore, DNA4, while somewhat immunogenic in terms of IFN-alpha induction, does not induce secretion of high amounts of IL-12 of IL-15. However, when combined in MM complexes, the cytokine signature is highly immunogenic. MM1 induces high levels of six cytokines, while MM2 induces measurable secretion of all seven cytokines. As discussed in the MM Stability subsection, the MM form stable complexes. These data thus imply uptake and processing of MM loaded with antigen cargo by PBMCs. The cytokines induced by MM all play critical and multi-faceted roles in coordinating the host immune response against both invading pathogens and tumor cells. Their functionality in the context of antitumor immunity is now briefly discussed.

Background on Measured Cytokines

IL-6 plays a pivotal role in the proliferation of activated cytotoxic lymphocytes (CTLs) by allowing dendritic cells (DCs) to overcome regulatory T cell (Treg) mediated suppression. IL-10, while previously thought to dampen the host immune response has recently been discovered to hold immune-potentiating properties via stimulating immune cells to secrete IFNγ, IL-18, IL-7, GM-CSF and IL-4. Indeed, patients treated with PEGylated IL-10 have increased numbers of activated circulating CTLs, as measured by PD-1+ and LAG-3+ gated flow cytometry. IL-12 enhances to cytotoxicity of NK cells, exhibits anti-angiogenic effects, and facilitates the priming of naïve T cells by enhancing activation of dendritic cells and inducing the secretion of TNF-alpha and INF-gamma. TNF-alpha enhances the short-term adaptive immune response by protecting DCs from being lysed via upregulation of the granzyme B inhibitor PI-9. Upregulation of PI-9 allows the same DC to conduct multiple rounds of T cells priming with the same epitope sequence rather than being lysed by recently primed CTLs. INF-alpha is a pleiotropic cytokine, which is best characterized in terms of potentiating antiviral immune responses. It is known enhance the activity of multiple immune subsets, including DCs, CTLs, NK cells and macrophages. It can induce secretion of interleukin-15, which is known to play a critical role in enhancing T cell function avidity and memory T cell formation. Lastly, IFN-gamma plays several key roles in enhancing antitumoral immunity. IFN-gamma is secreted by helper T cells to help polarize a cellular (Th1) rather than humoral (Th2) response, and it upregulates class I MHC expression, thereby increasing antigen presentation and hence, tumor cell recognition by cognate T cells.

These experiments establish the immunogenic potency of synthetic MM complexes, which are designed to mimic an infection by microbes loaded with tumor-specific and tumor associated antigens.

Example 5

In Vivo Activity of MM in the B16 Murine Melanoma Model

In vivo studies were conducted to evaluate the efficacy of MM using the well-characterized murine B16 melanoma model. B16 cells express the tissue-restricted melanoma differentiation antigen Trp2. MM were designed and synthesized to elicit an immune response against Trp2, by using polypeptide with the Trp2 epitope SVYDFFVWL (SEQ. ID NO. 8) embedded in the antigenic cargo. The aim of the experiment was to determine the effect of MM on tumor growth. The study was conducted as follows.

The RNA248/DNA4 adjuvant solution was produced by mixing 2 mg/mL solutions of RNA248 and DNA4 in PBS 1:1 to make a 1 mg/mL solution of RNA248/DNA4. Two different MM embodiments were used for experiments. The first employed MEL2 (SEQ. ID NO.5) as antigenic cargo, whereas the second employed MEL4 (SEQ. ID NO. 6) as antigenic cargo. To synthesize the MM, MEL2 or MEL4 were diluted in PBS at a stock concentrations of 1 mg/mL. For the MEL2 MM, MEL2 was titrated in 100 μL increments into an equal volume of RNA248/DNA4 adjuvant. For the MEL4 MM, MEL4 was titrated in 100 μL increments into an equal volume of RNA248/DNA4 adjuvant.

A total of twenty C57BL/6 mice were used for in vivo studies. Mice were divided into 4 groups of n=5 as follows:

Group #1: PBS Control
Group #2: RNA248/DNA4 Adjuvant Only
Group #3: MEL2 MM (RNA248/DNA4)+MEL2
Group #4: MEL4 MM (RNA248/DNA4)+MEL4

Tumors were initiated by inoculating all mice in the right hind flank with $10^5$ B16 melanoma cells on Day #4. Treatments began 4 full days after tumor inoculation on Day #0 according to the escalating dose schedule provided Table 4 below. For each treatment, mice were injected with a 33 gauge needle with either PBS (control), adjuvant only, MEL2 MM or MEL4 MM at the indicated dose.

TABLE 4

Dose Volume and Schedule

| Day | Dose Volume (uL) |
| --- | --- |
| 0 | 10 |
| 1 | 20 |
| 2 | 30 |
| 3 | 40 |
| 4 | 60 |
| 5 | 60 |
| 6 | 70 |
| 7 | 80 |
| 8 | 90 |
| 9 | 100 |
| 10 | 200 |

For injections, the total dose volume was divided equally between intradermal injections at the nape of the neck and intramuscular injections in the left hind flank.

Figure 19:
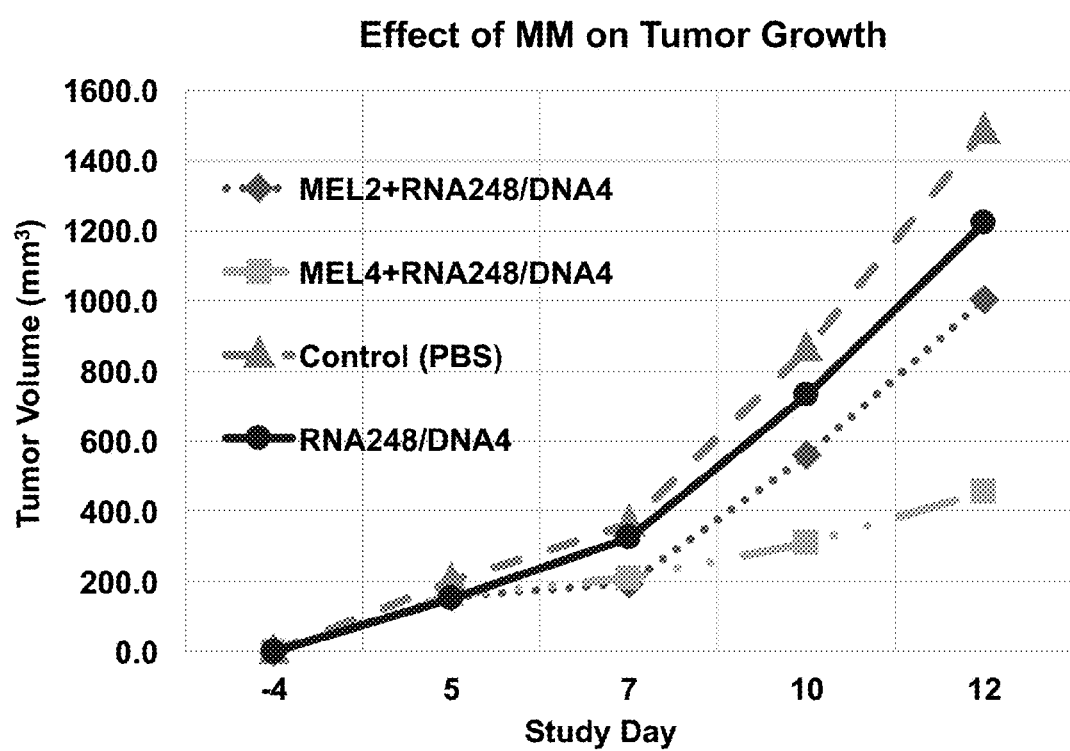
FIG. 19 is a plot showing the impact of MM on tumor growth in the well-established and aggressive B16 murine melanoma model. Data from four groups (n=5) is shown including a control group, an adjuvant (DNA4/RNA248) only, adjuvant+MEL2 (SVYDFFVWLRRHRKRR) MM and adjuvant+MEL4 (Pam(2)CSKKKKSVYDFFVWLRRHRKRR) MM treatment groups. Both MEL2 and MEL4 peptides include the SVYDFFVWL Trp2 epitope. While treatment with MEL2 and MEL4 MM inhibited tumor growth, MEL4 MM had the greatest impact, inhibiting tumor growth by 71% vs. control group at treatment day #12, 16 days post tumor implantation.

Tumors became measurable approximately 9 days after implantation, and subsequently tumors were measure 3×/weekly. Tumor volume was estimated by measuring the length and width with calipers and applying the formula: volume=0.5×length×width×width. The impact of MM on B16 tumor growth is demonstrated in FIG. 19, where the mean tumor volume for each group is plotted vs. study day. Compared to the control group, significant tumor growth inhibition was noted for both MM treatment groups, whereby MEL4 MM elicited the most potent tumor growth inhibition (71% at Day 12 relative to control.) Only minimal tumor growth inhibition was observed in the adjuvant only treatment group. The data demonstrate that MM inhibit tumor growth in vivo, in a model where the antigenic cargo contains a tissue-restricted antigen, namely Trp2. It is anticipated that further growth inhibition or tumor regression could be achieved by combining MM with immune checkpoint inhibitors with activity against PD-1, PD-L1, and/or CTLA-4. These in vivo studies demonstrate that MM monotherapy exhibits potent tumor growth inhibition.

The invention claimed is:

1. A method for treating cancer by administering to a patient with cancer immunogenic complexes comprised of a RNA comprising the sequence of SEQ. ID NO. 1 and a tumor-specific or tumor-associated polypeptide of 8 to 35 amino acids covalently bound to a RRHRKRR (SEQ. ID NO. 7) linker sequence at the amino terminus or carboxy terminus.

2. The method of claim 1, wherein additional immunostimulatory molecules selected from the group consisting of gardiquimod, resiquimod, Poly(I:C), Poly-ICLC, STING agonists, or CpG DNA are included in the immunogenic complex.

3. The method of claim 1, wherein a lipopeptide selected from the group consisting of Pam(2)CSK4 or Pam(3)CSK4 is incorporated into the immunogenic complex through covalent conjugation to the RRHRKRR-modified polypeptide at the amino terminus.

4. The method of claim 1, wherein a lipopeptide selected from the group consisting of Pam(2)-cysteine or Pam(3)-cysteine is incorporated into the immunogenic complex through covalent conjugation to the RRHRKRR-modified polypeptide at the amino terminus.

5. The method of claim 1, wherein a lipopeptide selected from the group consisting of Pam(2)-cysteine-serine-serine or Pam(3)-cysteine-serine-serine is incorporated into the immunogenic complex through covalent conjugation to the RRHRKRR-modified polypeptide at the amino terminus.

6. The method of claim 1, wherein the immunogenic complexes are non-covalently complexed to DNA with the sequence of SEQ. ID NO. 2.

7. The method of claim 1, wherein the immunogenic complexes are non-covalently complexed to DNA with the sequence of SEQ. ID NO. 3.

8. The method of claim 1, wherein the immunogenic complexes are tuned across several orders of magnitude and specifically to dimensions similar in size to bacteria and viruses by titrating the concentrations of each component and varying the final concentration of each component in a suitable buffer.

9. The method of claim 1, wherein the immunogenic complexes are co-administered with other cancer therapies selected from a group of antibodies or fusion proteins which bind to the following cell surface signaling molecules: PD-1, PD-L1, LAG-3, TIM-3, CTLA-4, CD27, or CD137.

10. The method of claim 1, wherein the immunogenic complexes are used to activate and expand tumor-specific or tumor-associated T cells in vitro.

11. The method of claim 1, wherein the immunogenic complexes are admixed with autologous heat-killed or freeze-thaw killed tumor cells and administered to a human patient for the treatment of cancer.

12. The method of claim 1, wherein the immunogenic complexes are synthesized with a high tumor-antigen content, whereby of the total peptide mass, the mass of tumor-specific or tumor-associated polypeptides exceeds 30%.

13. The method of claim 1, wherein the immunogenic complexes are injected directly into a subject's tumor using a syringe and needle.

14. The method of claim 1, wherein the tumor-specific polypeptide sequence corresponds to a region of a mutated tumor-specific protein bearing a single non-synonymous amino acid substitution.

15. A method for treating cancer by administering to a patient with cancer immunogenic complexes comprised of a RNA comprising the sequence of SEQ. ID NO. 1 and a tumor-specific or tumor-associated polypeptide of 8 to 35 amino acids covalently bound to a RRHRKRR (SEQ. ID NO. 7) linker sequence at the amino terminus or carboxy terminus, whereby—a single amino acid at any position in SEQ. ID NO. 7 is conservatively substituted, and/or whereby a single nucleotide at any position in SEQ. ID NO. 1 is substituted by any other nucleotide.

16. A method for treating cancer by administering to a patient with cancer immunogenic complexes comprised of a RNA comprising the sequence of SEQ. ID NO. 1 and a tumor-specific or tumor-associated polypeptide of 8 to 35 amino acids covalently bound to a RRHRKRR (SEQ. ID NO. 7) linker sequence at the amino terminus or carboxy terminus, whereby exactly one amino acid at any position in SEQ. ID NO. 7 is substituted by either a histidine, lysine, arginine, or glycine amino acid.

* * * * *